United States Patent [19]

Wallner

[11] Patent Number: 5,223,394

[45] Date of Patent: Jun. 29, 1993

[54] RECOMBINANT DNA MOLECULE COMPRISING LYMPHOCYTE FUNCTION-ASSOCIATED ANTIGEN 3 PHOSPHATIDYLINOSITOL LINKAGE SIGNAL SEQUENCE

[75] Inventor: Barbara P. Wallner, Cambridge, Mass.

[73] Assignee: Biogen, Inc., Cambridge, Mass.

[21] Appl. No.: 335,688

[22] Filed: Apr. 10, 1989

[51] Int. Cl.[5] .......................... C12Q 1/68; C12N 15/00
[52] U.S. Cl. ......................................... 435/6; 435/91; 435/172.3; 435/320.1; 435/252.3; 536/23.5; 536/23.53; 935/6
[58] Field of Search ................. 435/6, 91, 172.3, 320, 435/252.3; 536/27; 935/6, 19, 29, 88

[56] References Cited

U.S. PATENT DOCUMENTS 4,956,281  9/1990  Wallner et al. .................... 435/69.3

FOREIGN PATENT DOCUMENTS

WO8901041  2/1989  PCT Int'l Appl. .

OTHER PUBLICATIONS

Maddon et al, *Cell*, vol. 47, Nov. 7, 1986, "The T4 Gene Encodes the AIDS Virus Receptor and is Expressed in the Immune System and The Brain," pp. 333-348.

J. D. Bangs, et al., "Rapid Processing of the Carboxyl Terminus of a Trypanosome Variant Surface Glycoptrotein", *Proc. Natl. Acad. Sci. USA*, 82, pp. 3207-3211 (1985).

J. C. Boothroyd, "Antigenic Variation in African Trypanosomes", *Ann Rev. Microbiol.*, 39, pp. 475-502 (1985).

I. W. Caras et al., "Signal for Attachment of a Phospholipid Membrane Anchor in Decay Accelerating Factor", *Science*, 238, pp. 1280-1283 (1987).

A. Conzelmann, et al., "Glycolipid Anchors are Attached to Thy-1 Glycoprotein Rapidly After Translation", *J. Biochem.*, 246, pp. 605-610 (1987).

M. L. Dustin, et al., "Anchoring Mechanisms for LFA-3 Cell Adhesion Glycoprotein at Membrane Surface", *Nature*, 329, pp. 846-848 (1987).

M. L. Dustin, et al., "Purified Lymphocyte Function-Associated Antigen 3 Binds to CD2 and Mediates T Lymphocyte Adhesion", *J. Exp. Med.*, 165, pp. 677-692 (1987).

M. A. J. Ferguson et al., "Glycosyl-Phosphatidylinositol Moiety that Anchors *Trypanosoma brucei* Variant Surface Glycoprotein to the Membrane", *Science*, 239, pp. 753-759 (1988).

M. A. J. Ferguson, et al., "Glycosyl-sn-1,2-dimyristylphosphatidylinositol is Covalently Linked to *Trypanosoma brucei* . . . ", *J. Biol. Chem.*, 260, pp. 14547-14555 (1986).

M. A. J. Ferguson and A. F. Williams, "Cell-Surface Anchoring of Proteins Via Glycosyl-Phosphatidylinositol Structures", *Ann. Rev. Biochem*, 57, pp. 285-320 (1988).

A. H. Futerman, et al., "Identification of Covalently Bound Inositol in the Hydrophobic Membrane-Anchoring Domain . . . ", *Biochem. Biophys. Res. Com.*, 129, pp. 312-317 (1985).

R. Haas, et al., "Identification of Amine Components in a Glycolipid Membrane-Binding Domain . . . ", *Biochem.*, 25, pp. 3098-3105 (1986).

(List continued on next page.)

Primary Examiner—Robert J. Hill, Jr.
Assistant Examiner—Laurie Scheiner
Attorney, Agent, or Firm—James F. Haley, Jr.; Denise L. Loring; Immac J. Thampoe

[57] ABSTRACT

DNA sequences derived from a phosphatidylinositol-linked form of lymphocyte function-associated antigen 3 ("LFA-3") are provided which code for a phosphatidylinositol linkage signalling sequence. The linkage signalling sequence may be linked to DNA coding for secretory proteins or polypeptides to obtain phosphatidylinositol-linked chimeric proteins or polypeptides. The chimeric proteins can be used to produce targeted drugs, to form micellular or liposomal drug delivery systems, or to improve the purification or screening of particular cells, proteins or DNA libraries.

15 Claims, 10 Drawing Sheets

OTHER PUBLICATIONS

A. A. Holder, "Carbohydrate is Linked Through Ethanolamine to the C-Terminal Amino Acid of *Trypanosoma brucei* Variant Surface Glycoprotein", *J. Biochem.*, 209, pp. 261-262 (1982).

P. W. Kuchel, et al., "Molecular Weights of the Thy-1 Glycoproteins from Rat Thymus and Brain in the Presence and Absence of Deoxycholate", *J. Biochem.*, 169, pp. 411-417 (1978).

M. G. Low, "Biochemistry of the Glycosyl-Phosphatidylinositol Membrane Protein Anchors", *J. Biochem.*, 224, pp. 1-13 (1987).

M. G. Low, et al., "Covalently Attached Phosphatidylinositol as a Hydrophobic Anchor for Membrane Proteins", *Trends. Biol. Sci.*, 11, pp. 212-215 (1986).

M. G. Low, et al., "Cell-Specific Heterogeneity in Sensitivity of Phosphatidylinositol-Anchored Membrane Antigens . . . ", *J. Immunol. Methods*, 113, pp. 101-111 (1988).

F. Sanchez-Madrid, et al., "Three Distinct Antigens Associated with Human T-Lymphocyte Mediated Cytolysis: LFA-1, LFA-2, and LFA-3", *Proc. Natl. Acad. Sci. USA*, 79, pp. 7489-7493 (1982).

B. Seed, "An LFA-3 cDNA Encodes a Phospholipid-Linked Membrane Protein Homologous to its Receptor CD2", *Nature*, 329, pp. 840-842 (1987).

B. Seed and A. Aruffo, "Molecular Cloning of the CD2 Angiten, the T-Cell Erythrocyte Receptor, by a Rapid Immunoselection Procedure", *Proc. Natl. Acad. Sci. USA*, 84, pp. 3365-3369 (1987).

B. M. Sefton and J. E. Buss, "The Covalent Modification of Eukaryotic Proteins wth Lipid", *J. Cell Bio.*, 104, pp. 1449-1453 (1987).

T. Seki et al., "The Human Thy-1 Gene: Structure and Chromosomal Location", *Proc Natl. Acad. Sci. USA*, 82, pp. 6657-6661 (1985).

W. A. Sewell, et al., "Molecular Cloning of the Human T-Lymphocyte Surface CD2 (T11) Antigen", *Proc. Natl. Acad Sci. USA*, 83, pp. 8718-8722 (1986).

D. H. Sherman, et al., "Qa-2 Antigen Encoded by Q7$^b$ is Biochemically Indistinguishable from Qa-2 Expressed on the Surface of C57BL/10 Mouse Spleen Cells", *J. Immunol.*, 140, pp. 138-142 (1988).

T. A. Springer, et al., "The Lymphocyte Function-Associated LFA-1, CD2, and LFA-3 Molecules; Cell Adhesion Receptors of the Immune System", *Ann. Rev. Immunol.*, 5, pp. 223-252 (1987).

A. G. D. Tse, et al., "A Glycophospholipid Tail at the Carboxyl Terminus fo the Thy-1 Glycoprotein of Neurons and Thymocytes", *Science*, 230, pp. 1003-1008 (1985).

B. P. Wallner, et al., "Primary Structure of Lymphocyte Function-Associated Antigen 3 (LFA-3)-The Ligand of the T Lymphocyte CD2 Glycoprotein", *J. Exp. Med.*, 166, pp. 923-932 (1987).

G. L. Waneck, et al., "Tissue-Specific Expression of Cell-Surface Qa-2 Antigen from a Transfected Q7$^b$ Gene of C57BL/10 Mice", *J. Exp. Med.*, 165, pp. 1358-1370 (1987).

G. L. Waneck, et al., "Molecular Mapping of Signals in the Qa-2 Antigen Required for Attachment of the Phosphatidylinositol . . . ", *Proc. Natl. Acad. Sci., USA*, 85, pp. 577-581 (1988).

G. L. Waneck, et al., "Conversion of a PI-Anchored Protein to an Integral Membrane Protein by a Single Amino Acid Mutation", *Science*, 242, pp. 697-699 (1988).

L. J. Wysocki and V. L. Sato, "Panning for Lymphocytes: A Method for Cell Selection", *Proc. Natl. Acad Sci. USA*, 75, pp. 2844-2848 (1978).

```
             M   V   A   G   S   D   A   G   R   A   L   G   V   L
HT16   CGACGAGCCATGGTTGCTGGGAGCGACGCGGGGCGGGCCCTGGGGGTCCT
       ||||||||||||||||||||||||||||||||||||||||||||||||||
P24    CGACGAGCCATGGTTGCTGGGAGCGACGCGGGGCGGGCCCTGGGGGTCCT
             M   V   A   G   S   D   A   G   R   A   L   G   V   L

S   V   V   C   L   L   H   C   F   G   F   I   S   C   F   S   Q
HT16   CAGCGTGGTCTGCCTGCTGCACTGCTTTGGTTTCATCAGCTGTTTTTCCC   100
       ||||||||||||||||||||||||||||||||||||||||||||||||||
P24    CAGCGTGGTCTGCCTGCTGCACTGCTTTGGTTTCATCAGCTGTTTTTCCC   100
         S   V   V   C   L   L   H   C   F   G   F   I   S   C   F   S   Q

Q   I   Y   G   V   V   Y   G   N   V   T   F   H   V   P   S
HT16   AACAAATATATGGTGTTGTGTATGGGAATGTAACTTTCCATGTACCAAGC
       ||||||||||||||||||||||||||||||||||||||||||||||||||
P24    AACAAATATATGGTGTTGTGTATGGGAATGTAACTTTCCATGTACCAAGC
           Q   I   Y   G   V   V   Y   G   N   V   T   F   H   V   P   S

N   V   P   L   K   E   V   L   W   K   K   Q   K   D   K   V   A
HT16   AATGTGCCTTTAAAAGAGGTCCTATGGAAAAAACAAAAGGATAAAGTTGC   200
       ||||||||||||||||||||||||||||||||||||||||||||||||||
P24    AATGTGCCTTTAAAAGAGGTCCTATGGAAAAAACAAAAGGATAAAGTTGC   200
         N   V   P   L   K   E   V   L   W   K   K   Q   K   D   K   V   A

E   L   E   N   S   E   F   R   A   F   S   S   F   K   N   R   V
HT16   AGAACTGGAAAATTCTGAATTCAGAGCTTTCTCATCTTTTAAAAATAGGG
       ||||||||||||||||||||||||||||||||||||||||||||||||||
P24    AGAACTGGAAAATTCTGAATTCAGAGCTTTCTCATCTTTTAAAAATAGGG
           E   L   E   N   S   E   F   R   A   F   S   S   F   K   N   R   V

Y   L   D   T   V   S   G   S   L   T   I   Y   N   L   T   S
HT16   TTTATTTAGACACTGTGTCAGGTAGCCTCACTATCTACAACTTAACATCA   300
       ||||||||||||||||||||||||||||||||||||||||||||||||||
P24    TTTATTTAGACACTGTGTCAGGTAGCCTCACTATCTACAACTTAACATCA   300
         Y   L   D   T   V   S   G   S   L   T   I   Y   N   L   T   S
```

FIG. 1A

```
              S   D   E   D   E   Y   E   M   E   S   P   N   I   T   D   T   M
HT16      TCAGATGAAGATGAGTATGAAATGGAATCGCCAAATATTACTGATACCAT
          |||||||||||||||||||||||||||||||||||||||||||||||||
P24       TCAGATGAAGATGAGTATGAAATGGAATCGCCAAATATTACTGATACCAT
              S   D   E   D   E   Y   E   M   E   S   P   N   I   T   D   T   M

K   F   F   L   Y   V   L   E   S   L   P   S   P   T   L   T   C
HT16      GAAGTTCTTTCTTTATGTGCTTGAGTCTCTTCCATCTCCCACACTAACTT   400
          |||||||||||||||||||||||||||||||||||||||||||||||||
P24       GAAGTTCTTTCTTTATGTGCTTGAGTCTCTTCCATCTCCCACACTAACTT   400
            K   F   F   L   Y   V   L   E   S   L   P   S   P   T   L   T   C

A   L   T   N   G   S   I   E   V   Q   C   M   I   P   E   H
HT16      GTGCATTGACTAATGGAAGCATTGAAGTCCAATGCATGATACCAGAGCAT
          |||||||||||||||||||||||||||||||||||||||||||||||||
P24       GTGCATTGACTAATGGAAGCATTGAAGTCCAATGCATGATACCAGAGCAT
              A   L   T   N   G   S   I   E   V   Q   C   M   I   P   E   H

Y   N   S   H   R   G   L   I   M   Y   S   W   D   C   P   M   E
HT16      TACAACAGCCATCGAGGACTTATAATGTACTCATGGGATTGTCCTATGGA   500
          |||||||||||||||||||||||||||||||||||||||||||||||||
P24       TACAACAGCCATCGAGGACTTATAATGTACTCATGGGATTGTCCTATGGA   500
              Y   N   S   H   R   G   L   I   M   Y   S   W   D   C   P   M   E

Q   C   K   R   N   S   T   S   I   Y   F   K   M   E   N   D   L
HT16      GCAATGTAAACGTAACTCAACCAGTATATATTTTAAGATGGAAAATGATC
          |||||||||||||||||||||||||||||||||||||||||||||||||
P24       GCAATGTAAACGTAACTCAACCAGTATATATTTTAAGATGGAAAATGATC
              Q   C   K   R   N   S   T   S   I   Y   F   K   M   E   N   D   L

P   Q   K   I   Q   C   T   L   S   N   P   L   F   N   T   T
HT16      TTCCACAAAAAATACAGTGTACTCTTAGCAATCCATTATTTAATACAACA   600
          |||||||||||||||||||||||||||||||||||||||||||||||||
P24       TTCCACAAAAAATACAGTGTACTCTTAGCAATCCATTATTTAATACAACA   600
              P   Q   K   I   Q   C   T   L   S   N   P   L   F   N   T   T

S   S   I   I   L   T   T   C   I   P   S   S   G   H   S   R   H
HT16      TCATCAATCATTTTGACAACCTGTATCCCAAGCAGCGGTCATTCAAGACA
          |||||||||||||||||||||||||||||||||||||||||||||||||
P24       TCATCAATCATTTTGACAACCTGTATCCCAAGCAGCGGTCATTCAAGACA
            S   S   I   I   L   T   T   C   I   P   S   S   G   H   S   R   H

R   Y   A   L   I   P   I   P   L   A   V   I   T   T   C   I   V
HT16      CAGATATGCACTTATACCCATACCATTAGCAGTAATTACAACATGTATTG   700
          |||||||||||||||||||||||||||||||||||||||||||||||||
P24       CAGATATGCACTTATACCCATACCATTAGCAGTAATTACAACATGTATTG   700
            R   Y   A   L   I   P   I   P   L   A   V   I   T   T   C   I   V
```

FIG. 1B

```
              L   Y   M   N   G   I   L   K   C   D   R   K   P   D   R   T
HT16    TGCTGTATATGAATGGTATTCTGAAATGTGACAGAAAACCAGACAGAACC
        ||||||||||||||||||||||||   ||||   |||  ||   |||
P24     TGCTGTATATGAATGGTATGTATGCTTTTTAAAACAAAATAGTTTGAAAA
              L   Y   M   N   G   M   Y   A   F   *

N   S   N   *
HT16    AACTCCAATTGATTGGTAACAGAAGATGAAGACAACAGCATAACTAAATT      800
          ||    |  |  ||  |  |  ||    |  |      ||   ||
P24     CTTGCATTGTTTTCCAAAGGTCAGAAAATAGTTTAAGGATGAAAATAAAG      800

HT16    ATTTTAAAAACTAAAAAGCCATCTGATTTCTCATTTGAGTATTACAATTT
        ||  ||     |   |  |  |    |||     |     |    |||
P24     TTTGAAATTTTAGACATTTGAAAAAAAAAAAAAAAAAAAAAAAAAAAGCG

HT16    TTGAACAACTGTTGGAAATGTAACTTGAAGCAGCTGCTTTAAGAAGAAAT      900
P24     GCCGC                                                   900

HT16    ACCCACTAACAAAGAACAAGCATTAGTTTTGGCTGTCATCAACTTATTAT

HT16    ATGACTAGGTGCTTGCTTTTTTTGTCAGTAAATTGTTTTTACTGATGATG     1000

HT16    TAGATACTTTTGTAAATAAATGTAAATATGTACACAAGTG               1040
```

FIG. 1C

```
1    GCGGCCGCCGACGAGCCATGGTTGCTGGGAGCGACGCGGGGCGGGCCCTGGGGGTCCTCAGCGTGGTCTGCCTGCTGCACTGCTTTGGTTTCATCAGCTG   100
                       MetValAlaGlySerAspAlaGlyArgAlaLeuGlyValLeuSerValValCysLeuLeuHisCysPheGlyPheIleSerCy

101  TTTTTCCCAACAAATATATGGTGTTGTGTATGGGAATGTAACTTTCCATGTACCAAGCAATGTGCCTTTAAAAGAGGTCCTATGGAAAAAACAAAAGGAT   200
     sPheSerGlnGlnIleTyrGlyValValTyrGlyAsnValThrPheHisValProSerAsnValProLeuLysGluValLeuTrpLysLysGlnLysAsp

201  AAAGTTGCAGAACTGGAAAATTCTGAATTCAGAGCTTTCTCATCTTTTAAAAATAGGGTTTATTTAGACACTGTGTCAGGTAGCCTCACTATCTACAACT   300
     LysValAlaGluLeuGluAsnSerGluPheArgAlaPheSerSerPheLysAsnArgValTyrLeuAspThrValSerGlySerLeuThrIleTyrAsnL

301  TAACATCATCAGATGAAGATGAGTATGAAATGGAATCGCCAAATATTACTGATACCATGAAGTTCTTTCTTTATGTGCTTGAGTCTCTTCCATCTCCCAC   400
     euThrSerSerAspGluAspGluTyrGluMetGluSerProAsnIleThrAspThrMetLysPhePheLeuTyrValLeuGluSerLeuProSerProTh

401  ACTAACTTGTGCATTGACTAATGGAAGCATTGAAGTCCAATGCATGATACCAGAGCATTACAACAGCCATCGAGGACTTATAATGTACTCATGGGATTGT   500
     rLeuThrCysAlaLeuThrAsnGlySerIleGluValGlnCysMetIleProGluHisTyrAsnSerHisArgGlyLeuIleMetTyrSerTrpAspCys

501  CCTATGGAGCAATGTAAACGTAACTCAACCAGTATATATTTTAAGATGGAAAATGATCTTCCACAAAAAATACAGTGTACTCTTAGCAATCCATTATTTA   600
     ProMetGluGlnCysLysArgAsnSerThrSerIleTyrPheLysMetGluAsnAspLeuProGlnLysIleGlnCysThrLeuSerAsnProLeuPheA

601  ATACAACATCATCAATCATTTTGACAACCTGTATCCCAAGCAGCGGTCATTCAAGACACAGATATGCACTTATACCCATACCATTAGCAGTAATTACAAC   700
     snThrThrSerSerIleIleLeuThrThrCysIleProSerSerGlyHisSerArgHisArgTyrAlaLeuIleProIleProLeuAlaValIleThrTh

701  ATGTATTGTGCTGTATATGAATGGTATGTATGCTTTTTAAAACAAAATAGTTTGAAAACTTGCATTGTTTTCCAAAGGTCAGAAAATAGTTTAAGGATGA   800
     rCysIleValLeuTyrMetAsnGlyMetTyrAlaPhe

801  AAATAAAGTTTGAAATTTTAGACATTTGAAAAAAAAAAAAAAAAAAAAAAAAAAAGCGGCCGC  863
```

FIG. 2

```
   1  MetAsnArgGlyValProPheArgHisLeuLeuLeuAlaLeuAlaLeuGlnLeuValLeuProAlaAlaThrGlnGlyLysLysValValLeuGlyLysLysG
 101  lyAspThrValGluLeuThrCysThrAlaSerGlnLysLysSerIleGlnPheHisTrpLysAsnSerAsnGlnIleLysIleLeuGlyAsnGlnGlySe
 201  rPheLeuThrLysGlyProSerLeuAsnAspArgAlaAspSerArgArgSerLeuTrpAspGlnGlyAsnPheProLeuIleIleLysAsnLeuLys
 301  IleGluAspSerAspThrTyrIleCysGluValGluAspGlnLysGluGluValGlnLeuLeuValPheGlyLeuThrAlaAsnSerAspThrHisLeuL
 401  euGlnGlyGlnSerLeuThrLeuThrLeuGluSerProProGlySerSerProSerValGlnCysArgSerProArgGlyLysAsnIleGlnGlyGlyLy
 501  sThrLeuSerValSerGlnLeuGluLeuGlnAspSerGlyThrTrpThrCysThrValLeuGlnAsnGlnLysLysValGluPheLysIleAspIleVal
 601  ValLeuAlaPheGlnLysAlaSerSerIleValTyrLysLysGluGlyGluGlnValGluPheSerPheProLeuAlaPheThrValGluLysLeuThrG
 701  lySerGlyGluLeuTrpTrpGlnAlaGluArgAlaSerSerSerLysSerTrpIleThrPheAspLeuLysAsnLysGluValSerValLysArgValTh
 801  rGlnAspProLysLeuGlnMetGlyLysLysLeuProLeuHisLeuThrLeuProGlnAlaLeuProGlnTyrAlaGlySerGlyAsnLeuThrLeuAla
 901  LeuGluAlaLysThrGlyLysLeuHisGlnGluValAsnLeuValValMetArgAlaThrGlnLeuGlnLysAsnLeuThrCysGluValTrpGlyProT
1001  hrSerProLysLeuMetLeuSerLeuLysLeuGluAsnLysGluAlaLeuValSerLysArgGluLysAlaValTrpValLeuAsnProGluAlaGlyMe
2001  tTrpGlnCysLeuLeuSerAspSerGlyGlnValLeuLeuGluSerAsnIleLysValLeuProThrTrpSerThrProValGlnProMetAlaLeuIle
3001  ValLeuGlyValAlaGlyLeuLeuLeuPheIleGlyLeuGlyIlePhePheCysValArgCysArgHisArgArgArgGlnAlaGluArgMetSerG
4001  lnIleLysArgLeuLeuSerGluLysLysThrCysGlnCysProHisArgPheGlnLysThrCysSerProIle
```

FIG. 3

```
  1    ATGAACCGGGGAGTCCCTTTTAGGCACTTGCTTCTGGTGCTGCAACTGGC
       MetAsnArgGlyValProPheArgHisLeuLeuLeuValLeuGlnLeuAl

GCTCCTCCCAGCAGCCACTCAGGGAAAGAAAGTGGTGCTGGGCAAAAAAG    100
       aLeuLeuProAlaAlaThrGlnGlyLysLysValValLeuGlyLysLysG

101    GGGATACAGTGGAACTGACCTGTACAGCTTCCCAGAAGAAGAGCATACAA
       lyAspThrValGluLeuThrCysThrAlaSerGlnLysLysSerIleGln

TTCCACTGGAAAAACTCCAACCAGATAAAGATTCTGGGAAATCAGGGCTC    200
       PheHisTrpLysAsnSerAsnGlnIleLysIleLeuGlyAsnGlnGlySe

201    CTTCTTAACTAAAGGTCCATCCAAGCTGAATGATCGCGCTGACTCAAGAA
       rPheLeuThrLysGlyProSerLysLeuAsnAspArgAlaAspSerArgA

GAAGCTTGTGGGACCAAGGAAACTTTCCCCTGATCATCAAGAATCTTAAG    300
       rgSerLeuTrpAspGlnGlyAsnPheProLeuIleIleLysAsnLeuLys

301    ATAGAAGACTCAGATACTTACATCTGTGAAGTGGAGGACCAGAAGGAGGA
       IleGluAspSerAspThrTyrIleCysGluValGluAspGlnLysGluGl

GGTGCAATTGCTAGTGTTCGGATTGACTGCCAACTCTGACACCCACCTGC    400
       uValGlnLeuLeuValPheGlyLeuThrAlaAsnSerAspThrHisLeuL

401    TTCAGGGGCAGAGCCTGACCCTGACCTTGGAGAGCCCCCCTGGTAGTAGC
       euGlnGlyGlnSerLeuThrLeuThrLeuGluSerProProGlySerSer

CCCTCAGTGCAATGTAGGAGTCCAAGGGGTAAAAACATACAGGGGGGGAA    500
       ProSerValGlnCysArgSerProArgGlyLysAsnIleGlnGlyGlyLy

501    GACCCTCTCCGTGTCTCAGCTGGAGCTCCAGGATAGTGGCACCTGGACAT
       sThrLeuSerValSerGlnLeuGluLeuGlnAspSerGlyThrTrpThrC

GCACTGTCTTGCAGAACCAGAAGAAGGTGGAGTTCAAAATAGACATCGTG    600
       ysThrValLeuGlnAsnGlnLysLysValGluPheLysIleAspIleVal

601    GTGCTAGCTTTCCAGAAGGCCTCCAGCATAGTCTATAAGAAAGAGGGGGA
       ValLeuAlaPheGlnLysAlaSerSerIleValTyrLysLysGluGlyGl
```

FIG. 4A

```
                ACAGGTGGAGTTCTCCTTCCCACTCGCCTTTACAGTTGAAAAGCTGACGG   700
                uGlnValGluPheSerPheProLeuAlaPheThrValGluLysLeuThrG

701        GCAGTGGCGAGCTGTGGTGGCAGGCGGAGAGGGCTTCCTCCTCCAAGTCT
                lySerGlyGlyLeuTrpTrpGlnAlaGluArgAlaSerSerSerLysSer

TGGATCACCTTTGACCTGAAGAACAAGGAAGTGTCTGTAAAACGGGTTAC   800
                TrpIleThrPheAspLeuLysAsnLysGluValSerValLysArgValTh

801        AAGACACAGATATGCACTTATACCCATACCATTAGCAGTAATTACAACAT
                rArgHisArgTyrAlaLeuIleProIleProLeuAlaValIleThrThrC

GTATTGTGCTGTATATGAATGGTATGTATGCTTTTTAAAACAAAATAGTT   900
                ysIleValLeuTyrMetAsnGlyMetTyrAlaPhe

901        TGAAAACTTGCATTGTTTTCCAAAGGTCAGAAAATAGTTTAAGGATGAAA

ATAAAGTTTGAAATTTTAGACATTTGAAAAAAAAAAAAAAAAAAAAAAA   1000
     1001       AAAGCGGCC 1009
```

FIG. 4B

```
  1 ATGAACCGGGGAGTCCCTTTAGGCACTTGCTTCTGGTGCTGCAACTGGGCTCCTCCAGCAGCCACTCAGGAAAGAAAGTGGTGCTGCAAAAAG   100
    MetAsnArgGlyValProPheArgHisLeuLeuValLeuLeuAlaAlaThrGlnGlyLysLysValValLeuGlnLysLysG

101 GGGATACAGTGGAACTGACCTGTACAGCTTCCAGAAGAAGAGCATACAATTCACTGGAAAACTCCAACCAGATAAAGATTCTGGAAATCAGGGCTC   200
    lyAspThrValGluLeuThrCysThrAlaSerGlnLysLysSerIleGlnPheThrGlyLysLeuAsnGlnIleLysGlyAsnGlnGlySe

201 CTCTTAACTAAAGGTCATCAAGCTGAATGATCGGCTGACTCAAGAAGAAGCTTGTGGGACCAAGGAAACTTTCCCTGATCATCAAGAATCTTAAG   300
    rPheLeuThrLysGlyProSerLysLeuAsnAspArgAlaAspSerArgArgSerLeuTrpAspGlnPheProLeuIleIleLysAsnLeuLys

301 ATAGAAGACTCAGATACTTACATCTGTGAAGTGGAGGACCAGAAGGAGGTGCAATTGCTAGTGTTCGGATTGACTGCCAACTCTGACACCCACTGC   400
    IleGluAspSerAspThrTyrIleCysGluValGluAspGlnLysGluValGlnLeuLeuValPheGlyLeuThrAlaAsnSerAspThrHisLeuL

401 TTCAGGGGCAGAGCCTGACCCTGAGAGCCCCCTCAGTGAGTAGCCCCTCAATGTAGGAGTCCAAGGGGTAAAACATACAGGGGGGAA   500
    euGlnGlyGlnSerLeuThrLeuArgLeuGluSerProProSerValGlnCysArgSerProArgGlyLysAsnIleGlnGlyGlyLy

501 GACCCTCTCCGTGTCTCAGCTGAGCTGAGCTCCAGGATAGTGGCACCTGAGACATGGCACCTGTCTGCAGAACCAGAAGAGGTGAGTTCAAATAGACATGTG   600
    sThrLeuSerValSerGlnLeuGluLeuGlnAspSerGlyThrTrpThrCysThrValLeuGlnAsnGlnLysLysValGluPheLysIleAspIleVal
```

FIG. 5A

601 GTGCTAGCTTTCCAGAAGGCCTCCAGCATAGTCTATAAGAAAGAGGGGAACAGTGGAGTTCTCCTCCACTGCCTTCGAAAAGCTGACGG
    ValLeuAlaPheGlnLysAlaSerIleValTyrLysLysGluGlyGluGlyGlnValGluPheSerPheProLeuAlaPheThrValGluLysLeuThrG 700

701 GCAGTGGCGAGCTGTGGTGCAGGCGGAGAGGGCTTCCTCCTCCAAGTCTTGATCACCTTTGACCTGAAGAACAAGGAAGTGTCTAAAACGGGTTAT
    lySerGlyLeuTrpTrpTrpGlnAlaGluArgAlaSerSerLysSerLeuIleThrPheAspLeuLysAsnLysGluValSerLysThrGlyVallle 800

801 TAGCAATCCATTATTAATACAACATCATCAATCATTTTGACAACCTGTATCCCAAGCAGCGGTCATTCAAGACACAGATATGCACTTATACCCATACCA
    eSerAsnProLeuPheAsnThrThrSerSerIleIleLeuPheLeuThrThrCysIleProSerSerArgHisSerArgTyrAlaLeuIleProIlePro 900

901 TTAGCAGTAATTACAACATGTATTGTGCTGTATATGAATGTATGTTTTAAACAAATAGTTTGAAACTTTGAAAACTTGCATTGTTTTCCAAGGTCAGA
    LeuAlaValIleThrThrCysIleValLeuTyrMetAsnGlyMetTyrAlaPhe 1000

1001 AAATAGTTTAAGGATGAAATAAAGTTTGAAATTTTAGACATTTGAAAAAAAAAAAAAAAAAAAAAAAAAGCCGCC 1078

FIG. 5B

RECOMBINANT DNA MOLECULE COMPRISING LYMPHOCYTE FUNCTION-ASSOCIATED ANTIGEN 3 PHOSPHATIDYLINOSITOL LINKAGE SIGNAL SEQUENCE

The present invention relates to glycosyl phosphatidylinositol ("PI") linkage structures, which in vivo covalently anchor certain proteins to the surface of the cells in which they are produced. More particularly, the present invention relates to the isolation of DNA sequences coding for the phosphatidylinositol linkage signalling sequence of lymphocyte function-associated antigen 3 ("LFA-3"), and to processes for providing PI linkage structures to extracellular proteins (or the extracellular portion of membrane proteins), thereby giving such proteins a PI-linked form, with resulting advantages such as releasable plasma membrane binding, enhanced purifiability, the capability of micelle formation, etc. The invention also relates to novel chimeric polypeptides having PI linkage structures, hybrid DNA sequences encoding such polypeptides, and to products, methods and compositions made possible by the discoveries detailed herein.

BACKGROUND OF THE INVENTION

Proteins produced by expression of cellular DNA may be divided into three general groups: Cytoplasmic proteins, which remain wholly within the cell; extracellular or "soluble" proteins, which are secreted outside the cell; and membrane proteins, which become attached to the phospholipid bilayer of the cell membrane.

Different membrane proteins play major roles in a wide range of cell functions, such as anchoring cytoskeletal components, mediating cell-to-cell adhesion, transporting molecules into and out of the cell, receiving signals from hormones and other chemical transmitters, and many others.

Membrane proteins are bound to the plasma membrane in a variety of ways. Peripheral or "extrinsic" proteins do not penetrate the phospholipid bilayer but instead interact with the polar head groups on one surface of the bilayer or interact with other membrane proteins anchored directly to the bilayer. Integral or "intrinsic" proteins have a region which interacts with the hydrophobic core of the bilayer. Transmembrane proteins, such as cell surface antigens, cellular receptors, adhesion molecules and transport proteins, traverse the bilayer one or more times, exposing both cytoplasmic and extracellular regions or domains.

A further possibility for attachment to the plasma membrane is via covalent linkages between the lipid bilayer and the protein. In particular, a number of cell surface proteins are anchored to the cell membrane through a C-terminal, covalently attached glycosylated phosphatidylinositol moiety. See, e.g., Low et al., *Trends Biochem. Sci.*, 11, 212-15 (1986). The glycosyl phosphatidylinositol linkage, or "PI" linkage, is believed to be the anchoring structure for more than two dozen specific membrane proteins, found in a wide distribution of species and cell types See, Ferguson et al., *Ann. Rev. Biochem.*, 57, 285-320 (1988) (incorporated herein by reference). The biological functions of these PI-linked proteins are also highly diverse, including surface hydrolases, coat proteins, surface antigens and adhesion molecules.

The C-terminal amino acid residue of the PI-linked protein is attached to the membrane phosphatidylinositol moiety via an ethanolamine-phosphodiester-glycan bridge. Ferguson et al., *Science,* . 239, 753-759 (1988); Low, *Biochem. J.,* 244, 1-13 (1987) (incorporated herein by reference). The mechanism of attachment is thought to involve processing of a C-terminal hydrophobic sequence present on the precursor protein but eliminated prior to the PI anchoring of the mature protein. Ferguson et al., supra, *Ann. Rev. Biochem.*, 57, at 301-304. The processed C-terminal segments are believed to be a signal for phosphatidylinositol attachment. In one study, DNA coding for the 37-amino acid C-terminal sequence of the PI-linked protein, decay accelerating factor (DAF), was fused to the 3' end of DNA coding for a normally secreted protein fragment of glycoprotein D (from herpes simplex virus-1), resulting in a PI-linked fusion protein. See, Caras et al., *Science* 238, 1280–1283 (1987). However, comparison of the C-terminal sequences of many precursors of PI-linked proteins has failed to reveal a consensus PI linkage signalling sequence. See, Low, supra, FIG. 3; Ferguson et al., supra, *Ann. Rev. Biochem.*, 57, Table 3.

Although there has been a considerable amount of investigation of phosphatidylinositollinked proteins and the phosphatidylinositol linkage, there is a need for further characterization of specific PI linkages and for further investigation into the signal and mechanism for PI attachment to the cellular membrane, as well as the selective release of membrane bound proteins. These needs are addressed by the present invention, relating to the PI linkage structure of a PI-linked form of lymphocyte function-associated antigen 3 ("LFA-3"), and to applications of PI linkage signalling sequences derived from PI-linked LFA-3.

The PI linkage signalling sequences of the present invention, when linked in frame to the 3' end of DNA coding for a secreted polypeptide, or the secreted portion of a polypeptide, result on expression in a PI-linked form of the polypeptide. Using the DNA sequences and methods herein, novel chimeric proteins bearing a C-terminal phosphatidylinositol structure and numerous applications for such products are made possible.

SUMMARY OF THE INVENTION

Accordingly, it is an object of the present invention to provide DNA sequences coding for a phosphatidylinositol linkage signalling sequence.

It is a further object of the present invention to provide DNA sequences coding on expression for novel polypeptides having a C-terminal phosphatidylinositol linkage structure.

It is a further object of the present invention to provide novel PI-linked polypeptides and to provide a means for synthesizing a PI-linked form of soluble proteins or of the extracellular domains of integral membrane proteins.

It is a further object of the present invention to provide micelles of novel polypeptides bearing intact phosphatidylinositol linkage structures and to provide liposomes having surface characteristics determined by PI-linked polypeptides according to this invention.

It is a further object of the present invention to provide a means for altering the surface protein complement of cell cultures and to provide host cells capable of expressing PI-linked forms of exogenous proteins or polypeptides.

It is a further object of this invention to provide methods for directing cell-to-cell adhesion or targeting specific cells, for screening cells, and for directing the action or increasing the specificity of proteins and therapeutic agents.

These and other objects which will be apparent from the following description are accomplished herein by the discovery of DNA sequences coding for a lymphocyte function-associated antigen 3 phosphatidylinositol linkage signalling sequence, and DNA sequences which code on expression for polypeptides coded for on expression by such DNA sequences.

BRIEF DESCRIPTION OF THE DRAWINGS

FIG. 1 depicts a comparison of the DNA insert carried in phage λP24 (and the deduced amino acid sequence); which contains a coding region for PI-linked LFA-3, and the DNA insert carried in phage λHT16 (and the deduced amino acid sequence), which contains a coding region for the transmembrane form of LFA-3.

FIG. 2 depicts the DNA coding sequence and the deduced amino acid sequence of PI-linked LFA-3, with underscoring indicating a phosphatidylinositol linkage signalling sequence.

FIG. 3 depicts the amino acid sequence of natural CD4 protein, a surface antigen on T-cells. The putative signal sequence and the transmembrane region are indicated by underscoring.

FIG. 4 depicts the DNA coding sequence contained in plasmid T4/LFA-3/AD and coding for a fusion protein characterized by an extracellular domain of recombinant CD4 protein and a terminal sequence corresponding to the 28 C-terminal amino acids of PI-linked LFA-3. The deduced amino acid sequence of the chimeric protein is also indicated.

FIG. 5 depicts the DNA coding sequence contained in plasmid T4/LFA-3/2 and coding for a chimeric protein characterized by an extracellular domain of recombinant CD4 protein and a terminal sequence believed to represent a PI linkage signalling sequence according to the invention. The deduced amino acid sequence of the chimeric protein is also indicated. The fusion protein resulting from expression of this coding sequence in a transformed host is expected to yield a PI-linked form of CD4.

Figure 6A:
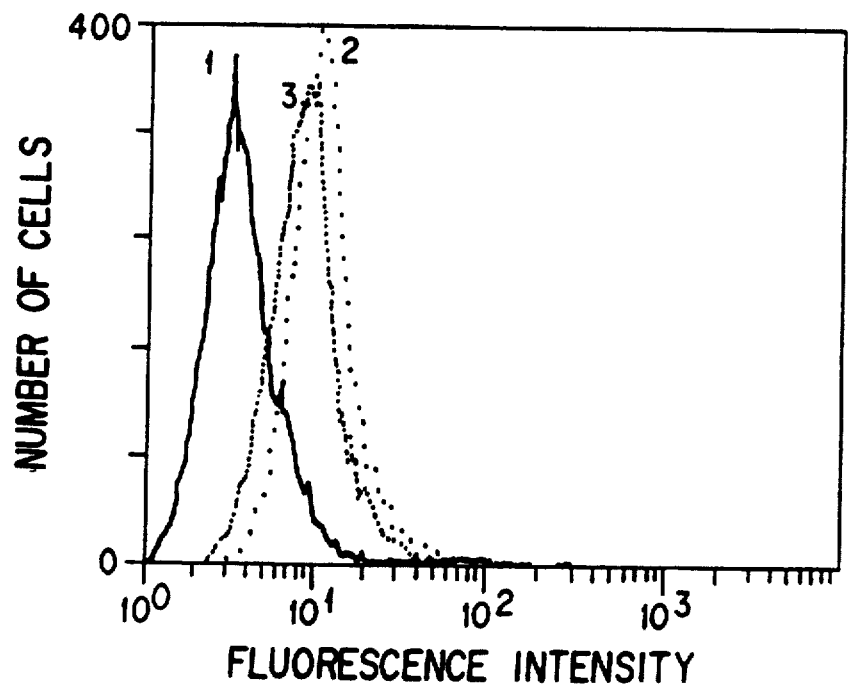
FIG. 6 is a graphic representation of an experiment to show that Clone #11 of CHO cells transfected with the hybrid DNA sequence T4/LFA-3/2 according to the invention produced a PI-linked CD4 protein, releasable from the cell surface by incubation with PIPLC.

sequences are derived from DNA coding for the PI-linked form of lymphocyte function-associated antigen 3 ("LFA-3") as described herein.

LFA-3 is a surface glycoprotein found on many cells, e.g., erythrocytes, monocytes, granuloctyes, cytotoxic T-lymphocytes, B-lymphoblastoid cells, smooth muscle cells, endothelial cells, fibroblasts. Springer et al., *Ann. Rev. Immunol.*, 5, 223-52(1987). LFA-3 binds to CD2 (a T-lymphocyte accessory molecule) and is believed to mediate adhesion of T-lymphocytes to target cells. This adhesion is essential to initiation of the T-lymphocyte functional response. Dustin et al., *J. Exp. Med.*, 165, 677-92 (1987).

LFA-3 occurs in two distinct cell surface forms: A transmembrane form and a PI-linked form. Dustin et al.., *Nature*, 329, 846–848 (1987). Comparison of cDNA sequences encoding the precursor polypeptides of both forms has revealed that the 5' ends of the sequences are identical but that the 3' ends of the sequences differ. See, commonly assigned, copending U.S. application Ser. No. 237,309, filed Aug. 26, 1988 (incorporated herein by reference) and FIG. 1 herein. The HT16 cDNA coding for the transmembrane form of LFA-3 contains a 3' segment (HT16 Nucleotides 655 through 723, FIG. 1) coding for a putative transmembrane region of 23 hydrophobic or uncharged amino acids and a 3' segment (HT16 Nucleotides 724 through 759, FIG. 1) coding for a putative cytoplasmic tail of 12 amino acids. The P24 cDNA coding for the PI-linked form of LFA-3 is shorter at the 3' end by thirty nucleotides, with 100% homology with the transmembrane form until the nucleotides coding for the last four amino acids (P24 Nucleotides 718 through 729, FIG. 1). Studies with transmembrane LFA-3 have demonstrated that removal of the 12-amino acid cytoplasmic domain converts the protein into a PI-linked protein. Therefore, it is theorized that the functional signal for phosphatidylinositol attachment is contained within the carboxy-terminal sequence of LFA-3.

The phosphatidylinositol linkage signalling sequences according to the present invention may be isolated from DNA coding for PI-linked LFA-3 or synthesized directly using standard techniques.

Preferred phosphatidylinositol linkage signalling sequences according to the present invention are derived from DNA coding for PI-linked LFA-3. Most preferably, the phosphatidylinositol linkage signalling sequence comprises the following:

```
5'-AGCAATCCATTATTTAATACAACATCATCAATCATTTTGACAACCTGT
ATCCCAAGCAGCGGTCATTCAAGACACAGATATGCACTTATACCCATACCA
TTAGCAGTAATTACAACATGTATTGTGCTGTATATGAATGGTATGTATGCT
TTT-3'.
``` invention produced a PI-linked CD4 protein, releasable from the cell surface by incubation with PIPLC.

DETAILED DESCRIPTION OF THE INVENTION

It has been discovered herein that a portion of the 3' end of cDNA coding for PI-linked LFA-3 can be isolated and linked, in turn, to the 3' end of a DNA sequence coding for a secreted polypeptide (or a secreted portion of a polypeptide) to confer PI linkage to the polypeptide. The 3' portion selected from the DNA coding for PI-linked LFA-3 which is able to confer PI linkage to a secreted polypeptide is referred to herein as a "phosphatidylinositol linkage signalling sequence." Preferably, the phosphatidylinositol linkage signalling The ability to attach a phosphatidylinositol structure according to this invention to an otherwise soluble protein or polypeptide leads to a wide variety of uses, some of which are discussed below:

I. Chimeric Polypeptides

The phosphatidylinositol linkage signalling sequences of the present invention may be used to construct hybrid DNA sequences coding for "chimeric" polypeptides having a PI linkage. As used herein, "chimeric" proteins or polypeptides will refer to proteins or polypeptides endowed with a PI structure in accordance with the teachings herein. A "chimeric protein" therefore will typically have a protein component (e.g., corresponding to a soluble protein) and a phosphatidylinositol component. Chimeric proteins are preferably the result of expression of the hybrid DNA molecules described herein. Such hybrid DNA molecules are advantageously prepared by linking the 5' end of a phosphatidylinositol linkage signalling sequence in the correct reading frame to the 3' end of a DNA segment coding for a secretory polypeptide or the secreted portion of a polypeptide. On expression in an appropriate host cell, a chimeric polypeptide or fusion protein is produced having an extracellular domain and a PI linkage anchoring it to the host cell membrane.

Suitable polypeptides for attachment of phosphatidylinositol structures according to this invention may be any polypeptide or fragment thereof which is normally secreted from the cell in which it is produced, or which can be made to be secreted by the attachment of a secretory signal sequence to the N-terminus. Suitable polypeptides will also include the extracellular portions of membrane-bound proteins, for example, where it is desired to produce a PI-linked form of a protein normally anchored to the cell surface via a transmembrane region and/or a cytoplasmic domain. Suitable types of polypeptides which may be advantageously provided with a phosphatidylinositol structure include cell surface ligands, antibodies to cell surface antigens, hormones, cytotoxins, cell activation ligands, soluble receptors, tumor markers, etc. In a particularly preferred embodiment, DNA encoding a truncated, soluble form of CD4 (also known as "T4"), a surface protein on helper T cells, is fused in frame with an LFA-3 phosphatidylinositol linkage signalling sequence according to this invention, to provide a novel chimeric protein having the CD4 receptor and a C-terminal phosphatidylinositol structure. (See, FIG. 3 herein.) DNA sequences coding for this fusion protein can be used to transform host cells, and culturing such hosts will result in a population of cells bearing PI-linked CD4 on the host surface membranes.

Since CD4 is now known to be a receptor to which the HIV virus (responsible for acquired immune deficiency syndrome) attaches in the process of infection, the chimeric CD4/phosphatidylinositol protein prepared as described herein offers a potential treatment for HIV infection: The CD4 receptor can be used to target the HIV virus; and through the PI linkage, the CD4 receptor can be expressed on cells which could destroy the virus. In like manner the CD4 receptor could be fused to a protein toxic to HIV infected cells (or other virus infected cells) and the PI structure employed in the formation of micelles or liposomes (discussed infra) to provide a high concentration drug delivery system.

PI-linked polypeptides are obtained using the hybrid DNA molecules according to the invention by expressing the hybrid DNA in a host capable of forming the phosphatidylinositol linkage. Any eukaryotic cell capable of forming a phosphatidylinositol linkage may be employed. The selection of host cell will be made on the basis of additional factors, such as stability of cell line, ease of culturing, compatability with other cells or organisms, cytotoxicity toward other cell types, and many other factors, depending on the final application envisioned for the PI-linked polypeptide produced by the transformation, or the application envisioned for the transformed cells themselves. Judicious selection of prospective host organisms will allow those skilled in the art to tailor the features of this invention to their diverse needs, while still relying on the principles described herein.

A wide variety of unicellular host cells and cell lines are suitable, including, for example, mammalian cell cultures, e.g., CHO, R1.1, B-W, and L-M cells, African green monkey cells (including COS1, COS7, BSC1, BSC40, and BMT10 cells), and human cells (including erythrocytes, monocytes, granuloctyes, cytotoxic T-lymphocytes, B-lymphoblastoid cells, smooth muscle cells, endothelial cells, fibroblasts, etc.), and cell lines developed from the foregoing.

The hybrid DNA molecules are expressed by operatively linking them to an expression control sequence in an appropriate expression vector, which in turn is used to transform an appropriate unicellular host. The operative linking of a hybrid DNA sequence of this invention to an expression control sequence includes the provision of a translation start signal in the correct reading frame upstream of the DNA sequence.

Many host-expression vector combinations may be employed in expressing the DNA sequences of this invention. Useful expression vectors may be constructed from segments of chromosomal, nonchromosomal or synthetic DNA. Suitable vectors include, for example, various known derivatives of SV40 and known bacterial plasmids, e.g., plasmids from E.coli including col E1, pCR1, pBR322, pMB9 and their derivatives, wider host range plasmids, e.g., RP4, phage DNAs (e.g., numerous derivatives of phage λ, such as NM989, and other DNA phages, such as M13 and Filamenteous single stranded DNA phages), yeast plasmids such as the 2μ plasmid or derivatives thereof, and vectors derived from combinations of plasmids and phage DNAs, such as plasmids which have been modified to employ phage DNA or other expression control sequences. For animal cell expression, plasmid BG312, a plasmid containing the major late promoter of adenovirus 2, is preferred.

In addition, any of a wide variety of expression control sequences—sequences that control the expression of a DNA sequence when operatively linked to it—may be used in these vectors to express the DNA sequence of this invention. Such useful expression control sequences include, for example, the early and late promoters of SV40 or the adenovirus, the lac system, the trp system, the TAC or TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells or their viruses, and various combinations thereof. For animal cell expression, it is preferred to use an expression control sequence derived from the major late promoter of adenovirus 2.

It should of course be understood that not all vectors and expression control sequences will function equally well to express the DNA sequences of this invention. Neither will all hosts function equally well with the same expression system. However, one of skill in the art may make a selection among these vectors, expression control sequences, and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the system, its controllability, and its compatibility with the particular DNA sequence, of this invention, particularly as regards potential secondary structures. Unicellular hosts should be selected by consideration of their compatibility with the chosen vector, the toxicity of the product coded on expression by the DNA sequences of this invention to them, their secretion characteristics, their ability to fold proteins correctly, their stability and culturing requirements, and the ease of purification of the products coded on expression by the DNA sequences of this invention.

Within these parameters one of skill in the art may select various vector/expression control system/host combinations that will express the DNA sequences of this invention.

Various agents are known to disrupt the phosphatidylinositol linkage and release the PI-linked protein from the cell surface. These include, for example, nitrous acid, phosphatidylinositol-specific phospholipases C ("PIPLC"), phosphatidyinosi-to-specific phospholipases D, and possibly endoglycosidase, phosophodiesterase and proteinase (Low, supra). PIPLC, e.g., from *Trypanosoma brucei*, has been the agent most extensivey studied. PIPLC irreversibly cleaves the PI linkage of PI-linked proteins with a high degree of specificity, creating a soluble protein. Thus, through the use of PIPLC or other agents which cleave the PI linkage, the PI-linked chimeric polypeptides according to the invention may be selectively released from the surface of the host cells in which they are produced.

The invention, therefore, provides a method for obtaining recombinant proteins in soluble form by culturing a host transformed with a hybrid DNA molecule to yield PI-anchored recombinant proteins, then introducing PIPLC or other agent to the culture medium, causing release of the protein in soluble form. Also contemplated are methods for purifying proteins which are difficult to purify by taking advantage of the releasable PI attachment to the cells in which they are produced. For instance, the host cells can be immobilized on a substrate by means of a surface receptor unrelated to the PI-linked protein, and then the protein can be eluted in soluble form using PIPLC or another phosphatidylinositol linkage-disrupting agent as an eluant.

II. Micelles

Chimeric proteins prepared according to the present invention and thus endowed with a terminal phosphatidylinositol structure can be purified with the phosphatidylinositol structure intact by solubilization of the membrane with detergents. In detergent solution, the chimeric proteins will generally be monomeric and evenly dispersed; however, removal of detergent by dialysis will cause aggregation of the phosphatidylinositol moieties to form micelles or iposomes.

Micelle formation can be induced and controlled by the addition of phosphoipids to achieve a specific ratio of protein to phospholipid. The orientation of the chimeric protein components of the micelles can be controlled also, so that the micelles have an outer surface which is predominantly composed of the phosphoipid moieties or predominantly composed of the protein moieties of the chimeric proteins. The size of the micelles may also be controlled by varying the detergent employed, the nature of the added phospholipid, or the phospholipid/protein ratio.

Generally, the size of liposomes directly affects the rate at which they are cleared from the bloodstream. For example, smaller liposomes and negatively charged iposomes appear to be more stable and accumulate in the spleen and liver. Thus, the micelles and liposomes prepared from chimeric proteins according to the present invention can be tailored to remain in the bloodstream for a desired period and to be delivered to specific organs. For example, small micelles according to the invention can be formed with an outer surface exhibiting a predominantly negative charge from the PI moiety, and such micelles would be ideal for delivering a particular protein moiety to the spleen or liver.

The chimeric protein micelles can also be structured so that the protein moiety is located on the outside. This type of structure leads to a high concentration of protein activity in the microenvironment surrounding the micelle. For, example, depending on the nature of the protein component of the micellular chimeric protein, the micelle can function as a multivalent ligand or receptor, or as a unitary protein having multiplied activity. Depending on the characteristics of the ligand-receptor interactions, the close proximity of, e.g., multiple ligands on the surface of a micelle according to the invention, could confer a several-fold higher affinity (due to lower on-off rate) for the ligand than that found for the monomeric ligand protein.

Many therapeutics are only effective when present in higher concentrations and must be injected in large doses to account for dilution and clearance effects. Mixed micelles can be engineered for drug targeting by including a second or third protein (to which the PI moiety has been attached) which specifically localizes the micelles to the target tissue or organ. For example, formation of a mixed micelle having chimeric ligand components and chimeric cytotoxic components, the former having an affinity for the surface receptor of a specific pathogen and the latter being toxic to the pathogen, produces a drug specifically targeted to the pathogen and also produces a therapeutic which localizes the effect of the cytotoxic component. The specific localization will assure a very high concentration of the drug at the site of interaction.

Proteins to be included in micelles can be cell targeting proteins (cell surface ligands, tumor markers, antibodies to tumor surface antigens, etc.), hormones, toxins, cell activation ligands, soluble receptors (e.g., CD4) or any other peptides or protein drugs.

Another approach to a mixed micelle is through the construction of a fusion protein to which the PI structure is attached. The fusion protein will exert plural functions, i.e., will exhibit plural domains corresponding to the protein fragments spliced together to form the fusion protein component. One part of such a fusion protein micelle component may act as a targeting protein (e.g., ligand of a specific receptor) while the other part of the protein may have a specific therapeutic function (e.g., a toxin that lyses specific cells; a cellular activator, a hormone, etc.).

III. Cell Targeting

The chimeric proteins according Lo this invention can be expressed in specific host cells and used to target that cell to specific tissues or organs.

As outlined above for the therapeutic applications of micelles, human cells with specific functions (killer cells, helper T-cells, etc.) can be engineered to be targeted to a specific site for action. Cytotoxic T-lymphocytes, natural killer cells, macrophages or other types of cells can be transfected with a PI-linked soluble receptor or ligand specific to the target cell (e.g., tumor cell marker transfected into cytotoxic T-lymphocytes). Such targeted cells may advantageously be cultured and specifically activated in vitro.

Most cell surface proteins are transmembrane proteins having a cytoplasmic domain. The cytoplasmic domain often transduces a cellular signal upon interaction with its extracellular ligand. However, by replacing the cytoplasmic domain with the PI linkage it is possible to attach the extracellular portion of the protein without its cytoplasmic signalling sequence and thus use that molecule strictly as a targeting molecule. Cell targeting in this fashion provides a number of cytolytic cells for site-specific action which normally do not show any specificity.

IV. Screening DNA Libraries

The sequence coding for the PI linkage can be incorporated in an expression vector and used to construct and screen a cDNA library for proteins which are normally secreted.

The phosphatidylinositol linkage signalling sequences of the present invention may be incorporated in expression vectors and used to construct and screen a cDNA library. In this feature, a PI linkage conferring sequence is included in the expression vector such that the cloned DNA coding for a normally secreted protein is anchored to the host cell surface on expression. The cells harboring the cloned DNA can then be separated, e.g., by the panning technique described by B. Seed and A. Aruffo, *Proc. Natl. Acad. Sci. USA*, 84, pp. 3365–3369 (1987) (incorporated herein by reference).

The cDNA library is preferably constructed using an animal cell expression vector which has been engineered so that each protein expressed has the PI linkage. The otherwise secreted proteins will thus be attached to the cell surface of the host cell, and cells expressing a particular protein of interest can be isolated using a monoclonal antibody to that protein. The isolation of cDNA for a secreted protein with monoclonal antibodies or a ligand for the protein by currently established techniques is very laborious and inefficient. The proposed technique therefore represents a great improvement in efficiency and reliability.

The following examples are provided in order to specifically illustrate the features of the present invention. Although the following description relates to a particularly preferred chimeric protein based on the extracellular domain of CD4, the examples are not intended to limit in any way the scope of the invention.

EXAMPLES

The following describes experiments to produce a PI-linked form of CD4 protein by attaching a terminal segment derived from DNA coding for PI-linked LFA-3 to DNA coding for a portion of the extracellular domain of CD4, which is normally (i.e., in wild type human T-cells) a membrane protein. CD4 is a glycoprotein of 458 amino acids, including a 23-amino acid signal sequence ($AA_1$ through $AA_{23}$), a 373-amino acid extracellular domain ($AA_{24}$ through $AA_{396}$), a transmembrane domain ($AA_{397}$ through $AA_{418}$), and a cytoplasmic tail ($AA_{419}$ through $AA_{458}$). The amino acid sequence for CD4 is shown in FIG. 3. See also, Littman et al., *Cell*, 55(4), p. 541 (1988). The putative signal sequence, extracellular domain, transmembrane domain and cytoplasmic domain are delineated by underscoring of the signal and transmembrane sequences.

Construction of a CD4/LFA-3 Expression Vector

In the following constructions, all restriction enzymes and other materials were used according to manufacturers' directions, unless otherwise specified.

DNA coding for PI-linked LFA-3 was obtained from plasmid P24, described in the aforementioned commonly assigned, copending U.S. application Ser. No. 237,309. An LB stab of *E.coli* cells carrying this plasmid was deposited in the In Vitro International, Inc. culture collection in Linthicum, MD on Jul. 22, 1988, under accession number IVI-10180.

Plasmid P24 containing the full length cDNA coding for PI-linked LFA-3 (see FIG. 2) was digested with restriction enzyme NotI (New England BioLabs, Beverly, MA) and the 849-base pair (bp) fragment isolated by electrophoresis on 1% agar gel. The 849 bp fragment (P24 insert in FIG. 1) was digested with restriction enzyme BbvI (New England BioLabs), and the 205 bp fragment ($N_{645}$-$N_{849}$ in FIG. 1) was isolated by electrophoresis, then blunt-ended with DNA polymerase 1 (Klenow fragment, New England BioLabs) and ligated into the unique BstEII restriction site of expression vector BG391 (accession no. IVI-10151, In Vitro International, Inc.), which incorporates a gene for a recombinant soluble CD4 protein corresponding to amino acids 1–325 in FIG. 3. See, PCT publication no. WO 89/01940.

The resulting recombinant DNA molecule, designated T4/LFA-3/AD, contained a DNA sequence coding for a polypeptide characterized by the N-terminal 267 amino acids of CD4, followed directly by the 28 C-terminal amino acids of PI-linked LFA-3. The coding sequence and deduced amino acid sequence of T4/LFA-3/AD is set forth in FIG. 4.

Plasmid T4/LFA-3/AD was linearized with XmnI and used to cotransfect CHO (DHFR$^-$) cells by the calcium phosphate method with the linearized StuI fragment of plasmid pAdD26, which carries the DHFR gene. See, Kaufman and Sharp, *Mol. Cell. Biol.*, 2, p. 1304 (1982). Transfected cells were grown and selected in alpha(−) Modified Eagles Medium (MEM) (Gibco).

Surface expression of CD4 transfected cells was determined by Fluorescence Activated Cell Sorter (FACS) analysis: $1 \times 10^6$ transfected cells and control CHO cells were removed from tissue culture dishes by incubation with Hank's BSS buffer, 0.5 EDTA at 4° C. for 15 minutes. The detached cells were then pelleted, resuspended in 50 μl of PBN buffer (1×PBS, 0.5% BSA, 0.1% sodium azide) and incubated with 100 μl of monoclonal antibody OKT4A (Becton Dickinson, Mountainview, CA) on ice for 45 minutes. The cells were pelleted by centrifugation and resuspended twice in PBN buffer. The cells were pelleted again and the cell pellets were resuspended in 100 μl of a 1:50 dilution of FCI (Fluorescein Conjugated Affinity Purified F (ab') 2 Fragment Sheep Anti-Mouse IgG; Cappel Biomedical, Westchester, PA) in PBN buffer and incubated on ice for 30 minutes. The cells were layered onto a cushion of 300 μl 100% fetal calf serum and then resuspended in 800 μl of 1×PBS buffer and the intensity of fluorescence measured by FACS (Becton Dickinson, Mountainview, CA).

By FACS analysis, 40 clones were obtained which were positive for surface expression of the chimeric CD4/LFA-3 polypeptide. Four positive clones were cultured in alpha(-) MEM and incubated with a 1:50 dilution of PIPLC (a generous gift of M. Low, Columbia University, New York, NY) in 100 μl MEM, at 37° C. for 30 minutes. $1 \times 10^6$ cells of each clone before and after PIPLC treatment were prepared for FACS analysis as above. The fluorescent intensities of the PIPLC treated clones were identical to the untreated clones, indicating that the CD4 protein was not released and that expression of the T4/LFA-3/AD plasmid did not result in a chimeric polypeptide having a simple phosphatidylinositol anchor.

A recombinant DNA molecule having a larger segment from the 3' end of LFA-3 cDNA was next constructed. Following the above procedure, a CD4/LFA-3 hybrid DNA sequence was prepared which coded for the N-terminal 266 amino acids of the extracellular domain of CD4 and the C-terminal 51 amino acids of PI-linked LFA-3. The ligation introduced an isoleucine residue. This hybrid DNA molecule was designated T4/LFA-3/2. The coding sequence and deduced amino acid sequence of T4/LFA-3/2 is set forth in FIG. 5.

Plasmid T4/LFA-3/2 was linearized with XmnI as above and used to cotransfect $2 \times 10^7$ CHO (DHFR$^-$) cells with StuI-linearized plasmid pAdD26 by the calcium phosphate method, as above. Transfected cells were grown and selected in alpha(−) MEM.

Figure 6B:
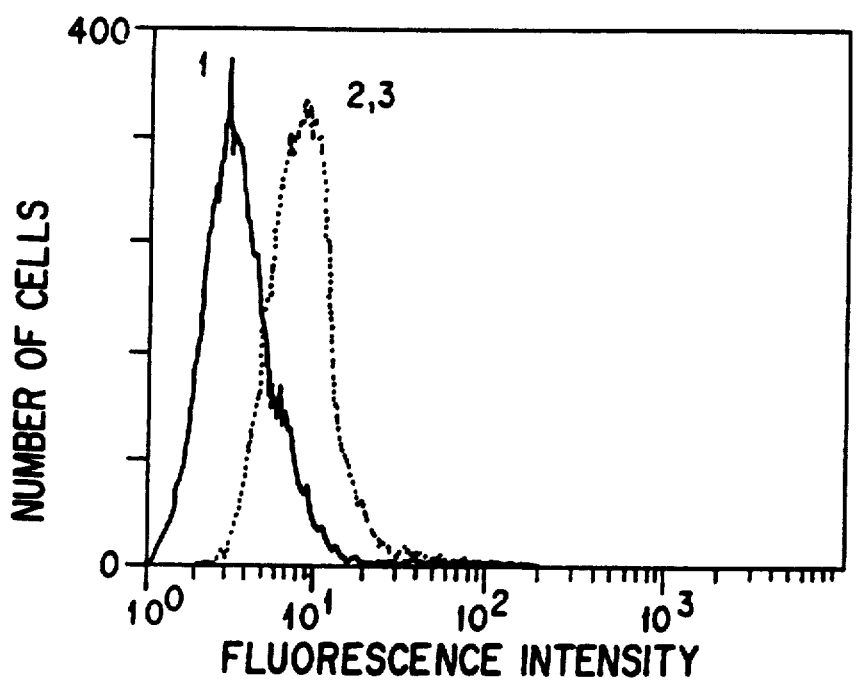

Sixteen resistant colonies were isolated, expanded and assayed for surface expression of a CD4 protein by FACS as described above. Four clones that were strongly positive for CD4 surface expression, T4/LFA-3/2 #3, #8, #11 and #15, were assayed further for release of surface CD4 after incubation with PIPLC, as described above. Two of the clones showed a decrease in surface CD4 after incubation with PIPLC, indicating that the extracellular portion of the CD4 protein was attached to the cell surface via a phosphatidylinositol linkage (conferred by expression of the 3' phosphatidylinositol linkage signalling sequence excised from the P24 cDNA); two clones did not show decreased surface expression in CD4 after incubation with PIPLC, indicating that the surface CD4 of those particular clones was not PI-linked. FIG. 6 shows in the form of graphs the results of the PIPLC incubations on Clone T4-LFA-3-2 #11 (positive for PI-linked CD4 expression) and Clone T4/LFA-3/2 #15 (control, negative for PI-linked expression).

Microorganisms and hybrid DNA molecules according to the invention are exemplified by a culture deposited in the In Vitro International, Inc. culture collection, 611 P. Hammonds Ferry Road, Linthicum, MD, on April 5, 1989. The culture is identified as follows:

| Plasmid | Culture | Accession No. |
| --- | --- | --- |
| T4/LFA-3/2 | E. coli JA221(pT4/LFA-3/2) | IVI-10202 |

This deposit was transferred to the American Type Culture Collection in Rockville, Md., on Jun. 20, 1991.

The transferred deposite has been assigned ATCC accession number 68789.

While the products and methods of the present invention have been described herein with reference to particular DNA sequences and polypeptides, a wide range of additional embodiments are contemplated. For instance, although the foregoing description refers to a specific CD4/LFA-3 construct, many similar constructs are apparent from the disclosure, including, for example, longer or shorter portions of the DNA sequence encoding the extracellular domain of CD4, linked to the preferred LFA-3 PI linkage signalling sequence. Also, PI linkage signalling sequences derived from the PI-linked form of LFA-3 which are longer or shorter than the specific sequence of the examples are contemplated, as are nonhomologous DNA sequences which, through the degeneracy of the genetic code, code on expression for the same operative C-terminal peptides as coded for by PI linkage signalling sequences derived directly from PI-linked LFA-3. The present invention of course also contemplates chimeric polypeptides characterized by N-terminal extracellular regions derived from soluble proteins or the extracellular portions of proteins other than CD4. All such additional embodiments and obvious modifications are within the intended scope of this invention as defined by the appended claims.

I claim:

1. A hybrid DNA molecule comprising (a) a first DNA molecule coding for a secreted protein, a portion of a secreted protein or an extracellular region of a membrane protein, and, downstream of said first DNA molecule, (b) a second DNA molecule coding for a lymphocyte function-associated antigen 3 phosphatidylinositol linkage signalling sequence operatively linked to said first DNA molecule such that expression of the hybrid DNA molecule results in a phosphatidylinositol-linked polypeptide.

2. The hybrid DNA molecule according to claim 1, wherein the second DNA molecule is selected from the group consisting of:

5'-AGCAATCCATTATTTAATACAACATCATCAATCATTTTGACAACCTGT
ATCCCAAGCAGCGGTCATTCAAGACACAGATATGCACTTATACCCATACCA
TTAGCAGTAATTACAACATGTATTGTGCTGTATATGAATGGTATGTATGCT TTT-3', and DNA molecules which are degenerate to the foregoing DNA molecule.

3. The hybrid DNA molecule according to claim 1, wherein the first DNA molecule codes for a protein or portion of a protein selected from the group consisting of cell surface ligands, antibodies to cell surface antigens, hormones, cytotoxins, cell activation ligands, surface proteases, soluble receptors, secreted proteins and extrinsic proteins.

4. The hybrid DNA molecule according to claim 3, wherein the first DNA molecule codes for an extracellular domain of CD4.

5. A recombinant DNA molecule comprising (a) a first DNA molecule coding for a secreted protein, a portion of a secreted protein or an extracellular region of a membrane protein, (b) a second DNA molecule downstream of said first DNA molecule coding for a lymphocyte function-associated antigen 3 phosphatidylinositol linkage signalling sequence and operatively linked to said first DNA molecule such that expression of the first and second DNA sequences results in a phosphatidylinositol-linked polypeptide, and (c) an expression control sequence operatively linked to the first DNA molecule.

6. The recombinant DNA molecule according to claim 5, wherein the second DNA, molecule is selected from the group consisting of:

5'-AGCAATCCATTATTTAATACAACATCATCAATCATTTTGACAACCTGT
ATCCCAAGCAGCGGTCATTCAAGACACAGATATGCACTTATACCCATACCA
TTAGCAGTAATTACAACATGTATTGTGCTGTATATGAATGGTATGTATGCTTTT-3', and DNA sequences which are degenerate to the foregoing DNA molecule.

7. The recombinant DNA molecule according to claim 5, wherein the first DNA molecule codes for a protein or portion of a protein selected from the group consisting of cell surface ligands, antibodies to cell surface antigens, hormones, cytotoxins, cell activation ligands, soluble receptors, surface proteases, secreted proteins and extrinsic proteins.

8. A recombinant DNA molecules according to claim 5, wherein the first DNA molecule codes for an extracellular domain of CD4.

9. The recombinant DNA molecule according to claim 7, wherein the expression control sequence is selected from the group consisting of early and late promoters of SV40 or adenovirus.

10. A eukaryotic host cell culture transfected with a recombinant DNA molecules comprising (a) a first DNA molecule coding for a secreted protein, a portion of a secreted protein or an extracellular region of a membrane protein, (b) a second DNA molecule downstream of said first DNA molecule coding for a lymphocyte function-associated antigen 3 phosphatidylinositol linkage signalling sequence and operatively linked to said first DNA molecule such that expression of the first and second DNA sequences results in a phosphatidylinositol-linked polypeptide, and (c) an expression control sequence operatively linked to the first DNA molecule.

11. A eukaryotic host cell culture according to claim 10, wherein the second DNA molecule is selected from the group consisting of:

5'-AGCAATCCATTATTTAATACAACATCATCAATCATTTTGACAACCTGT
ATCCCAAGCAGCGGTCATTCAAGACACAGATATGCACTTATACCCATACCA
TTAGCAGTAATTACAACATGTATTGTGCTGTATATGAATGGTATGTATGCTTTT-3', and DNA sequences which are degenerate to the foregoing DNA molecule.

12. The eukaryotic host cell culture according to claim 10, wherein the first DNA molecule codes for a protein or portion of a protein selected from the group consisting of cell surface ligands, antibodies to cell surface antigens, hormones, cytotoxins, cell activation lignads, soluble receptors, surface proteases, secreted proteins and extrinsic proteins.

13. The eukaryotic host cell culture according to claim 10, wherein the first DNA molecule codes for an extracellular domain of CD4.

14. The eukaryotic host cell culture according to claim 10, wherein the expression control sequence is selected from the group consisting of early and late promoters of SV40 or adenovirus.

15. The eukaryotic host cell culture according to claim 10, wherein the host cell is selected from the group consisting of CHO cells, R1.1 cells, COS cells, killer cells, helper T-cells, cytotoxic T-lymphocytes and macrophages.

* * * * *